United States Patent
Lei et al.

(10) Patent No.: US 12,357,832 B1
(45) Date of Patent: Jul. 15, 2025

(54) MULTIFUNCTIONAL PACEMAKER WIRE CONVERSION DEVICE AND APPLICATION METHOD THEREOF

(71) Applicant: Tongji Hospital, Tongji Medical College, Huazhong University of Science and Technology, Wuhan (CN)

(72) Inventors: Lei Lei, Wuhan (CN); Yan Wang, Wuhan (CN); Lin Wang, Wuhan (CN); Hesong Zeng, Wuhan (CN); Jiangtao Yan, Wuhan (CN); Chunxia Zhao, Wuhan (CN); Jiangang Jiang, Wuhan (CN); Liang Chen, Wuhan (CN); Yang Bai, Wuhan (CN); Mei Hu, Wuhan (CN)

(73) Assignee: Tongji Hospital, Tongji Medical College, Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 19/054,993

(22) Filed: Feb. 17, 2025

(30) Foreign Application Priority Data

Jul. 26, 2024 (CN) .......................... 202411011263.2

(51) Int. Cl.
*A61N 1/362* (2006.01)
(52) U.S. Cl.
CPC ................................... *A61N 1/362* (2013.01)
(58) Field of Classification Search
CPC ........................................................ A61N 1/32
USPC ............................................................... 607/9
See application file for complete search history.

(56) References Cited

U.S. PATENT DOCUMENTS

| | | | |
|---|---|---|---|
| 2003/0120327 A1* | 6/2003 | Tobritzhofer | A61N 1/05 607/116 |
| 2006/0111632 A1* | 5/2006 | Chen | A61F 5/0046 600/431 |
| 2016/0228060 A1* | 8/2016 | Mazar | A61B 5/282 |
| 2017/0157393 A1* | 6/2017 | Osypka | A61N 1/0563 |
| 2021/0228887 A1 | 7/2021 | Doerr et al. | |
| 2021/0244953 A1* | 8/2021 | Von Bergen | A61N 1/36 |

FOREIGN PATENT DOCUMENTS

CN 115487421 A 12/2022

* cited by examiner

*Primary Examiner* — Nicole F Johnson
(74) *Attorney, Agent, or Firm* — Nitin Kaushik

(57) ABSTRACT

The present invention provides a multifunctional pacemaker wire conversion device and an application method thereof. The device includes a box body, a permanent electrode female connector, a permanent electrode male connector, a temporary electrode female connector, a temporary electrode male connector, and a circuit line. A cavity is formed in the box body, the permanent electrode female connector, the permanent electrode male connector, the temporary electrode female connector, and the temporary electrode male connector are disposed on the box body, and the permanent electrode female connector, the permanent electrode male connector, the temporary electrode female connector, and the temporary electrode male connector are electrically connected to each other through the circuit line disposed in the cavity.

6 Claims, 10 Drawing Sheets

MULTIFUNCTIONAL PACEMAKER WIRE CONVERSION DEVICE AND APPLICATION METHOD THEREOF

CROSS-REFERENCE TO RELATED APPLICATIONS

The application claims priority to Chinese patent application No. 2024110112632, filed on Jul. 26, 2024, the entire contents of which are incorporated herein by reference.

TECHNICAL FIELD

The present invention relates to the technical field of pacemakers, and in particular, to a multifunctional pacemaker wire conversion device and an application method thereof.

BACKGROUND

A pacemaker is composed of a main unit and an electrode. In the prior art, pacemakers are classified into a temporary pacemaker and a permanent pacemaker according to the product functional design and the patient adaptive symptoms. The temporary pacemaker is mainly used to ensure the safety of the patient in emergency situations or in short periods of time, and can also serve as transitional therapy. The temporary pacemaker is mainly connected to the main unit placed outside the body through the electrode to maintain the life and stable heart rate of the patient. The retention time is usually no more than two weeks. The permanent pacemaker needs to be implanted into the body and carried for a long time. A pocket is created in the body, and the electrode is connected to the main unit through the heart and buried under the skin.

In an actual therapy scenario, to protect the life and health of the patient in time, when medical staff use the temporary pacemaker or the permanent pacemaker, there will be a situation where main units and electrodes of the temporary pacemaker and the permanent pacemaker are mixed and overlapped. However, since electrode wires and interfaces used by the temporary pacemaker and the permanent pacemaker are different, the pacemakers may fail to work normally after the main units and electrodes are mixed and overlapped.

Therefore, there is an urgent need for a multifunctional pacemaker wire conversion device, so that the permanent pacemaker and the temporary pacemaker can be freely combined with a permanent electrode or a temporary electrode for use.

SUMMARY

The present invention discloses a multifunctional pacemaker wire conversion device and an application method thereof, to solve a problem that how to provide a multifunctional pacemaker wire conversion device to enable a permanent pacemaker and a temporary pacemaker to be freely combined with a permanent electrode or a temporary electrode for use in the above background.

To solve the technical problem described above, technical solutions are provided as follows:

A multifunctional pacemaker wire conversion device, where a permanent pacemaker and a temporary pacemaker can be freely combined with a permanent electrode or a temporary electrode for use, and the device includes:

a box body, where a cavity is formed in the box body;

a permanent electrode female connector, disposed on the box body and configured to be connected to the permanent electrode;

a permanent electrode male connector, disposed on the box body and configured to be connected to the permanent pacemaker;

a temporary electrode female connector, disposed on the box body and configured to be connected to the temporary electrode;

a temporary electrode male connector, disposed on the box body and configured to be connected to the temporary pacemaker; and a circuit line, disposed in the cavity, where the permanent electrode male connector, the permanent electrode female connector, the temporary electrode male connector, and the temporary electrode female connector are electrically connected through the circuit line.

Preferably, the circuit line includes a positive crosslink point and a negative crosslink point;

positive electrodes of the permanent electrode male connector, the permanent electrode female connector, the temporary electrode male connector, and the temporary electrode female connector are electrically connected through the positive crosslink point; and negative electrodes of the permanent electrode male connector, the permanent electrode female connector, the temporary electrode male connector, and the temporary electrode female connector are electrically connected through the negative crosslink point.

Preferably, the permanent electrode female connector includes a permanent electrode female connector fixing member, a permanent electrode female connector positive terminal, and a permanent electrode female connector negative terminal;

the permanent electrode female connector fixing member is fixed on the box body, the permanent electrode female connector fixing member is of a tubular structure, a first end of the permanent electrode female connector fixing member is placed in the cavity, and a second end of the permanent electrode female connector fixing member is placed outside the box body;

the permanent electrode female connector positive terminal and the permanent electrode female connector negative terminal are sequentially disposed in the permanent electrode female connector fixing member, the permanent electrode female connector positive terminal is connected to the positive crosslink point, and the permanent electrode female connector negative terminal is connected to the negative crosslink point; and when the permanent electrode is inserted from the second end of the permanent electrode female connector fixing member, the permanent electrode female connector positive terminal is in contact with and is electrically connected to a positive electrode of the permanent electrode, and the permanent electrode female connector negative terminal is in contact with and is electrically connected to a negative electrode of the permanent electrode.

Preferably, the permanent electrode male connector includes a permanent electrode male connector fixing member, a permanent electrode male connector positive terminal, and a permanent electrode male connector negative terminal;

the permanent electrode male connector fixing member is fixed on the box body, the permanent electrode male connector fixing member is of a tubular structure, a first end of the permanent electrode male connector fixing member is placed in the cavity, and a second end of the permanent electrode male connector fixing member extends out of the box body;

the permanent electrode male connector positive terminal and the permanent electrode male connector negative terminal are coaxially disposed in the permanent electrode male connector fixing member, and the permanent electrode male connector positive terminal and the permanent electrode male connector negative terminal are separated through an insulating layer;

one end of each of the permanent electrode male connector positive terminal and the permanent electrode male connector negative terminal is fixedly disposed at the first end of the permanent electrode male connector fixing member, and the other end of each of the permanent electrode male connector positive terminal and the permanent electrode male connector negative terminal extends out of the box body from the second end of the permanent electrode male connector fixing member; and the positive crosslink point is connected to the permanent electrode male connector positive terminal, and the negative crosslink point is connected to the permanent electrode male connector negative terminal.

Preferably, the temporary electrode female connector includes a temporary electrode female connector positive terminal fixing member, a temporary electrode female connector negative terminal fixing member, a temporary electrode female connector positive terminal, and a temporary electrode female connector negative terminal;

both the temporary electrode female connector positive terminal fixing member and the temporary electrode female connector negative terminal fixing member are fixed on the box body, the temporary electrode female connector positive terminal fixing member and the temporary electrode female connector negative terminal fixing member are of a tubular structure, first ends of the temporary electrode female connector positive terminal fixing member and the temporary electrode female connector negative terminal fixing member are placed in the cavity, and second ends of the temporary electrode female connector positive terminal fixing member and the temporary electrode female connector negative terminal fixing member extend out of the box body;

the temporary electrode female connector positive terminal is disposed in the temporary electrode female connector positive terminal fixing member and is electrically connected to the positive electrode;

the temporary electrode female connector negative terminal is disposed in the temporary electrode female connector negative terminal fixing member and is electrically connected to the negative crosslink point; and when the temporary electrode is inserted from the second ends of the temporary electrode female connector positive terminal fixing member and the temporary electrode female connector negative terminal fixing member, the temporary electrode female connector positive terminal is in contact with a positive electrode of the temporary electrode, and the temporary electrode female connector negative terminal is in contact with a negative electrode of the temporary electrode.

Preferably, the temporary electrode male connector includes a temporary electrode male connector positive terminal fixing member, a temporary electrode male connector negative terminal fixing member, a temporary electrode male connector positive terminal, and a temporary electrode male connector negative terminal;

both the temporary electrode male connector positive terminal fixing member and the temporary electrode male connector negative terminal fixing member are fixed on the box body;

one end of the temporary electrode male connector positive terminal is fixedly disposed on the temporary electrode male connector positive terminal fixing member, and the other end of the temporary electrode male connector positive terminal extends out of the box body;

one end of the temporary electrode male connector negative terminal is fixedly disposed on the temporary electrode male connector negative terminal fixing member, and the other end of the temporary electrode male connector negative terminal extends out of the box body; and the positive crosslink point is electrically connected to the temporary electrode male connector positive terminal, and the negative electrode is electrically connected to the temporary electrode male connector negative terminal.

Preferably, the permanent electrode female connector positive terminal, the permanent electrode female connector negative terminal, the temporary electrode female connector positive terminal, and the temporary electrode female connector negative terminal are all of an annular structure, a plurality of groups of first elastic sheets are disposed on an inner side wall of the annular structure, and the plurality of groups of first elastic sheets are disposed along a circumference of the annular structure.

Preferably, the device further includes an elastic collet and a cover cap;

the elastic collet is disposed at the second end of each of the permanent electrode female connector fixing member, the temporary electrode female connector positive terminal fixing member, and the temporary electrode female connector negative terminal fixing member;

an outer wall of each of the permanent electrode female connector fixing member, the temporary electrode female connector positive terminal fixing member, and the temporary electrode female connector negative terminal fixing member is provided with a thread;

the cover cap is disposed on each of the permanent electrode female connector fixing member, the temporary electrode female connector positive terminal fixing member, and the temporary electrode female connector negative terminal fixing member through the thread;

when the cover cap is disposed on the permanent electrode female connector fixing member, the temporary electrode female connector positive terminal fixing member, or the temporary electrode female connector negative terminal fixing member, the cover cap abuts against the elastic collet, and the elastic collet contracts under an action of the cover cap; and the end cover is detachably disposed on the box body, the sealing ring is disposed between the end cover and the box body, and when the end cover is detachably disposed on the box body, the end cover abuts against the sealing ring, and the cavity forms a closed waterproof chamber.

The present invention further discloses a method for converting a single-chamber pacemaker into a dual-chamber pacemaker, where the multifunctional pacemaker wire conversion device according to any one of the above is applied, and the method includes:

performing cardiac evaluation on a heart of a patient, to determine a cardiac condition of the patient, where a first permanent electrode and a first permanent pacemaker connected to the first permanent electrode are implanted into a body of the patient; and selecting the dual-chamber pacemaker and an adapted second permanent electrode according to a cardiac evaluation result of the patient;

exposing the first permanent pacemaker implanted into the body of the patient through an incision;

connecting a temporary pacemaker to a temporary electrode male connector of the multifunctional pacemaker wire conversion device, disconnecting the first permanent electrode from the first permanent pacemaker, and connecting the first permanent electrode to a permanent electrode female plug of the multifunctional pacemaker wire conversion device;

implanting the second permanent electrode into the heart of the patient, and testing a working state of the second permanent electrode;

if the working state of the second permanent electrode is normal, connecting the second permanent electrode to the dual-chamber pacemaker;

then disconnecting the first permanent electrode from the multifunctional pacemaker wire conversion device, and removing the temporary pacemaker and the multifunctional pacemaker wire conversion device;

testing a working state of the first permanent electrode;

connecting the tested first permanent electrode to the dual-chamber pacemaker;

setting a parameter of the dual-chamber pacemaker, to adapt to the cardiac condition of the patient;

testing a function of the dual-chamber pacemaker, to ensure that the dual-chamber pacemaker paces the heart; and after it is determined that the dual-chamber pacemaker works normally, burying the dual-chamber pacemaker in the body of the patient, and suturing the incision.

The present invention further discloses a method for converting a single-chamber pacemaker into a cardiac resynchronization therapy pacemaker, where an original single-chamber pacemaker is converted into the cardiac resynchronization therapy pacemaker through the multifunctional pacemaker wire conversion device according to any one of the above, and the method includes:

performing cardiac evaluation on a heart of a patient, to determine a cardiac condition of the patient, where a first permanent electrode and a first permanent pacemaker connected to the first permanent electrode are implanted into a body of the patient; and selecting the cardiac resynchronization therapy pacemaker and an adapted third permanent electrode according to a cardiac evaluation result of the patient;

exposing the first permanent pacemaker implanted into the body of the patient through an incision;

connecting a temporary pacemaker to a temporary electrode male connector of the multifunctional pacemaker wire conversion device, disconnecting the first permanent electrode from the first permanent pacemaker, and connecting the first permanent electrode to a permanent electrode female connector of the multifunctional pacemaker wire conversion device; implanting the third permanent electrode into the heart of the patient; and testing a working state of the third permanent electrode;

if the working state of the third permanent electrode is normal, connecting the third permanent electrode to the cardiac resynchronization therapy pacemaker;

then disconnecting the first permanent electrode from the multifunctional pacemaker wire conversion device, and removing the temporary pacemaker and the multifunctional pacemaker wire conversion device;

testing a working state of the first permanent electrode;

connecting the tested first permanent electrode to the cardiac resynchronization therapy pacemaker;

setting a parameter of the cardiac resynchronization therapy pacemaker, to adapt to the cardiac condition of the patient;

testing a function of the cardiac resynchronization therapy pacemaker, to ensure that the cardiac resynchronization therapy pacemaker paces the heart; and after it is determined that the cardiac resynchronization therapy pacemaker works normally, burying the cardiac resynchronization therapy pacemaker in the body of the patient, and suturing the incision.

The present invention further discloses a method for reimplanting a permanent pacemaker, where the multifunctional pacemaker wire conversion device according to any one of the above is applied, and the method includes:

exposing a first permanent pacemaker implanted into a pocket of a patient through an incision;

connecting a temporary pacemaker to a temporary electrode male connector of the multifunctional pacemaker wire conversion device, disconnecting a first permanent electrode implanted into a heart of the patient from the first permanent pacemaker, and connecting the first permanent electrode to a permanent electrode female connector of the multifunctional pacemaker wire conversion device;

performing a debridement treatment on the pocket of the patient;

performing a disinfection treatment on the first permanent pacemaker;

disconnecting the first permanent electrode from the multifunctional pacemaker wire conversion device, and removing the temporary pacemaker and the multifunctional pacemaker wire conversion device;

reconnecting the first permanent pacemaker to the first permanent electrode; and reburying the first permanent pacemaker in the pocket of the patient, and suturing the incision.

The present invention further discloses an emergency treatment method when a patient is allergic to a permanent pacemaker, where the multifunctional pacemaker wire conversion device according to any one of the above is applied, and the method includes:

exposing a first permanent pacemaker implanted into a pocket of a patient through an incision;

connecting a temporary pacemaker to a temporary electrode male connector of the multifunctional pacemaker wire conversion device, disconnecting a first permanent electrode implanted into a heart of the patient from the first permanent pacemaker, and connecting the first permanent electrode to a permanent electrode female connector of the multifunctional pacemaker wire conversion device;

debriding the pocket of the patient, checking an allergen of the patient, and selecting a new permanent pacemaker according to the allergen of the patient;

disconnecting the first permanent electrode from the multifunctional pacemaker wire conversion device, and removing the temporary pacemaker and the multifunctional pacemaker wire conversion device;

connecting the new permanent pacemaker to the first permanent electrode; and reburying the new permanent pacemaker in the pocket of the patient, and suturing the incision.

Beneficial effects: The present invention provides a multifunctional pacemaker wire conversion device, including a box body, a permanent electrode female connector, a permanent electrode male connector, a temporary electrode female connector, a temporary electrode male connector, and a circuit line. A cavity is formed in the box body, the permanent electrode female connector, the permanent electrode male connector, the temporary electrode female connector, and the temporary electrode male connector are disposed on the box body, and the permanent electrode female connector, the permanent electrode male connector, the temporary electrode female connector, and the temporary electrode male connector are electrically connected to each other through the circuit line disposed in the cavity. The permanent electrode female connector is configured to be connected to a permanent electrode. The permanent electrode male connector is configured to be connected to a permanent pacemaker. The temporary electrode female connector is configured to be connected to a temporary electrode. The temporary electrode male connector is configured to be connected to a temporary pacemaker. During use, any one of the permanent pacemaker and the temporary pacemaker and any one of the permanent electrode and the temporary electrode are connected to the multifunctional pacemaker wire conversion device, so that the permanent pacemaker and the temporary pacemaker can be freely combined with the permanent electrode or the temporary electrode for use through the multifunctional pacemaker wire conversion device.

Figure 1:
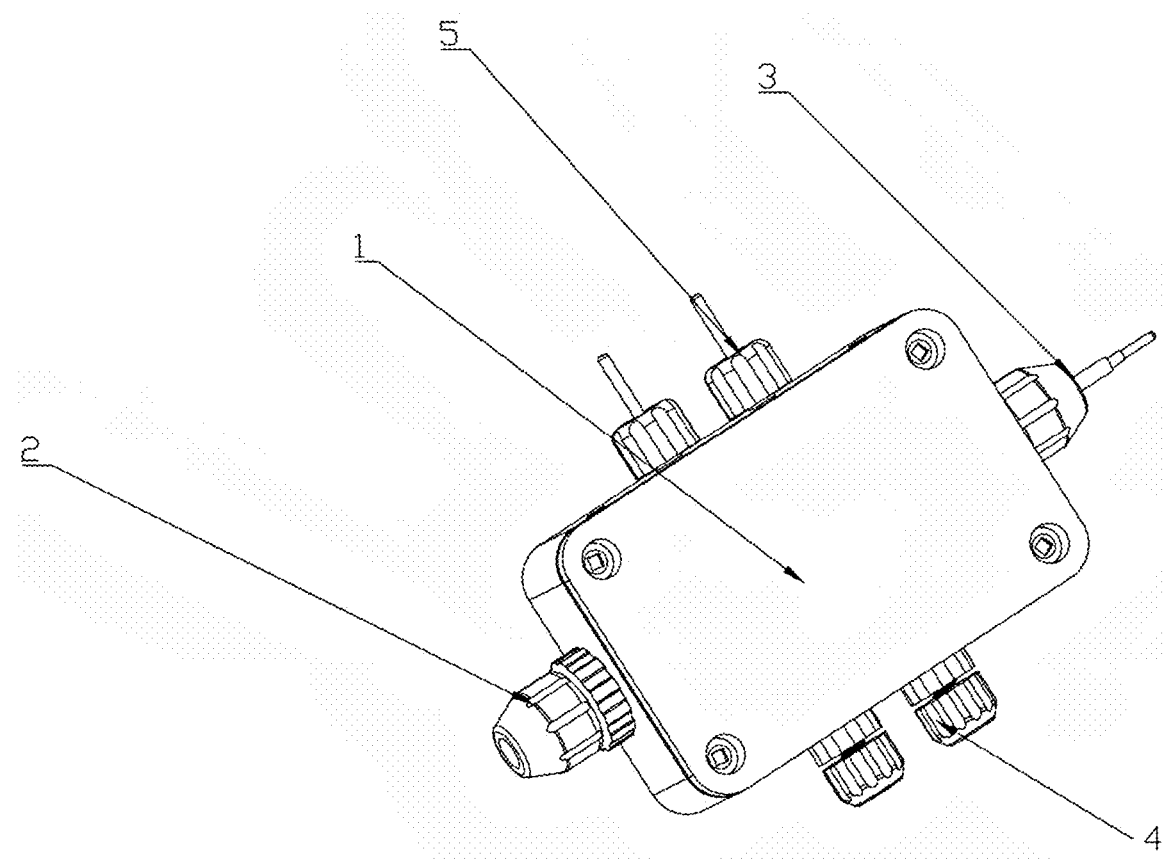
FIG. 1 is a schematic diagram of an overall structure of the present invention.

Reference numerals of main elements are as follows:
1. box body;
2. permanent electrode female connector; 21. permanent electrode female connector fixing member; 22. permanent electrode female connector positive terminal; 23. permanent electrode female connector negative terminal;
3. permanent electrode male connector; 31. permanent electrode male connector fixing member; 32. permanent electrode male connector positive terminal; 33. permanent electrode male connector negative terminal; 34. insulating layer;
4. temporary electrode female connector; 41. temporary electrode female connector positive terminal fixing member; 42. temporary electrode female connector negative terminal fixing member; 43. temporary electrode female connector positive terminal; 44. temporary electrode female connector negative terminal;
5. temporary electrode male connector; 51. temporary electrode male connector positive terminal fixing member; 52. temporary electrode male connector negative terminal fixing member; 53. temporary electrode male connector positive terminal; 54. temporary electrode male connector negative terminal;
6. circuit line; 61. positive crosslink point; 62. negative crosslink point;
7. first elastic sheet; 8. elastic collet; 9. cover cap; 10. sealing ring; 11. end cover.

DETAILED DESCRIPTION OF THE EMBODIMENTS

To make the objectives, technical solutions, and advantages of the embodiments of the present invention clearer, the following clearly and completely describes the technical solutions in the embodiments of the present invention with reference to the accompanying drawings in the embodiments of the present invention. Apparently, the described embodiments are some but not all of the embodiments of the present invention. Generally, assemblies, of the embodiments of the present invention, described and illustrated in the accompanying drawings herein may be arranged and designed in a variety of different configurations.

The detailed descriptions of the embodiments of the present invention provided in the accompanying drawings are not intended to limit the claimed protection scope of the present invention, but only to represent selected embodiments of the present invention. All other embodiments obtained by those of ordinary skill in the art based on the embodiments of the present invention without creative efforts shall fall within the protection scope of the present invention.

Figure 2:
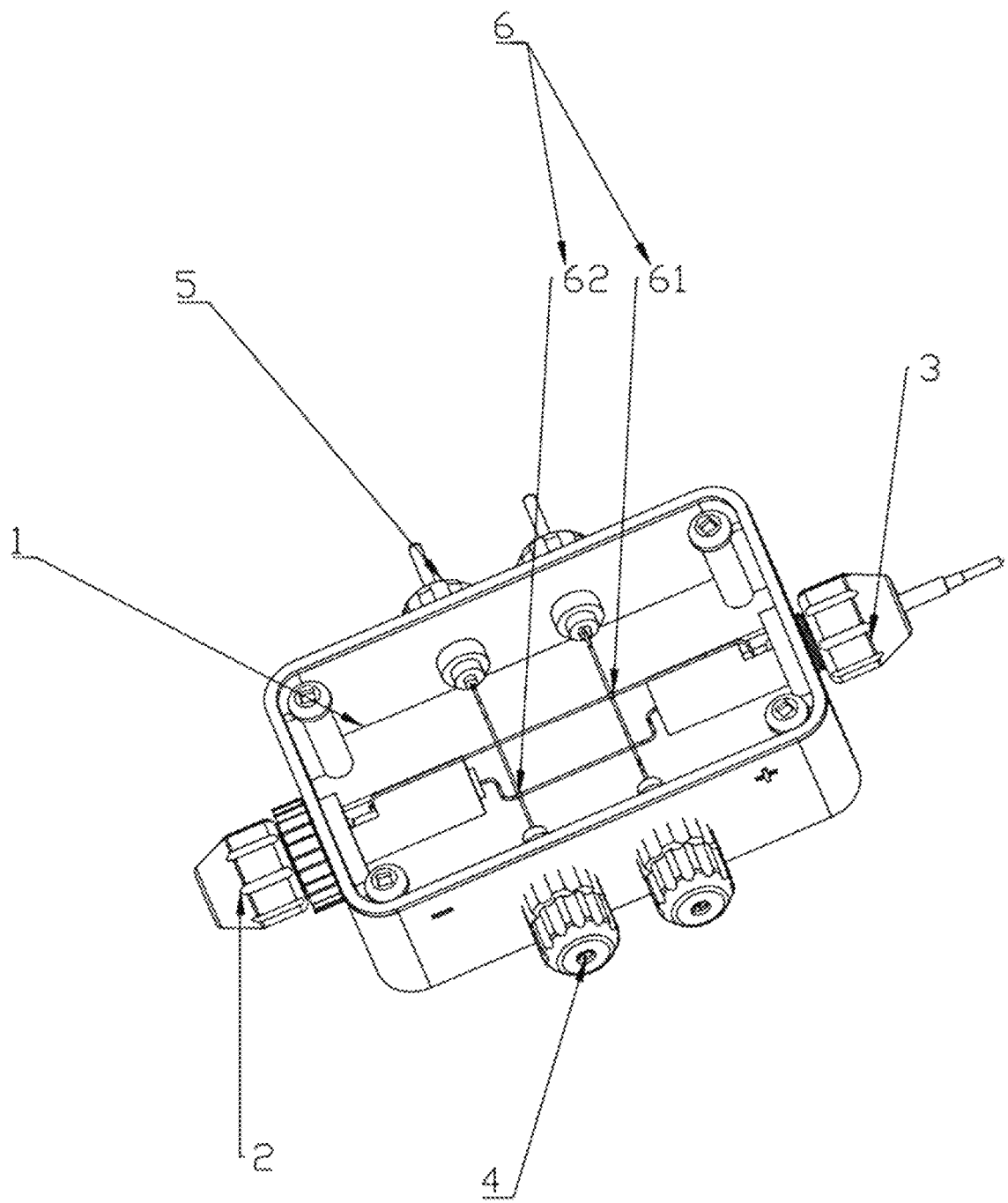
FIG. 2 is a diagram of an internal structure of an overall structure of the present invention.
Figure 3:
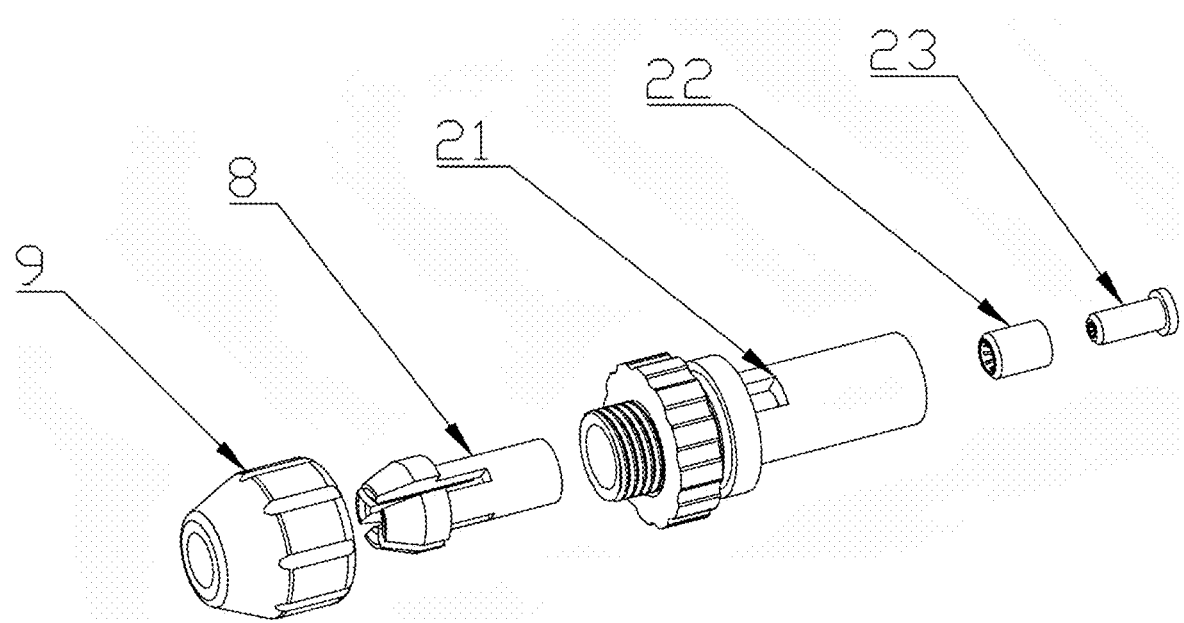
FIG. 3 is an exploded view of a permanent electrode female connector of the present invention.
Figure 4:
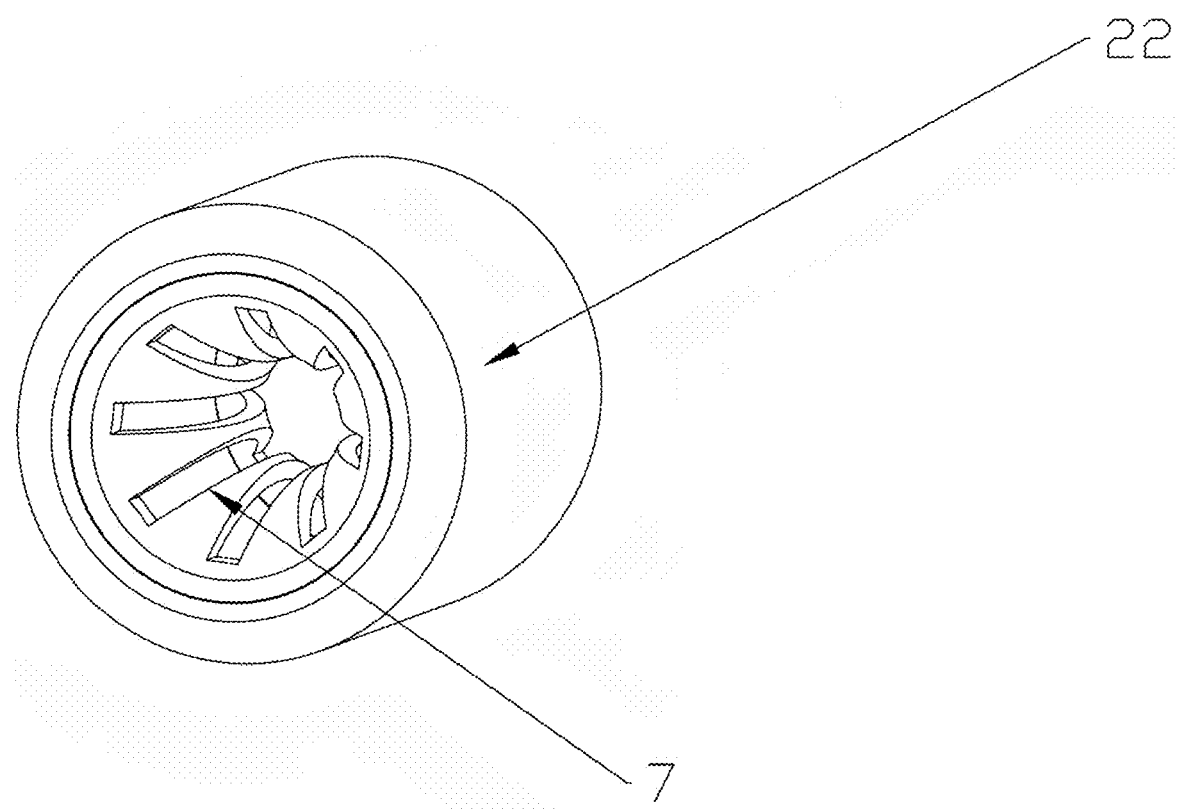
FIG. 4 is a schematic structural diagram of a permanent electrode female connector positive terminal of the present invention.
Figure 5:
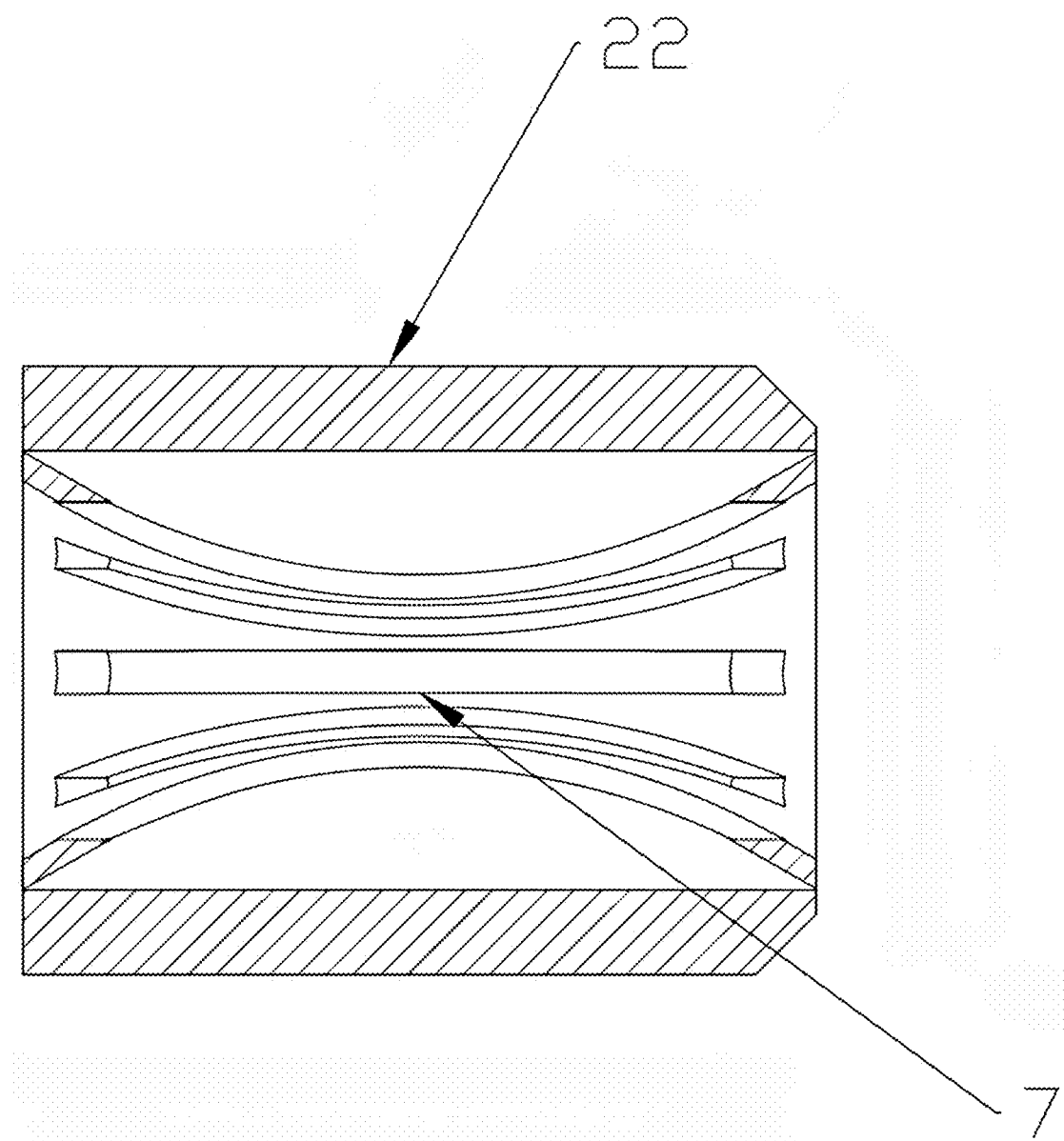
FIG. 5 is a sectional view of a permanent electrode female connector positive terminal of the present invention.
Figure 6:
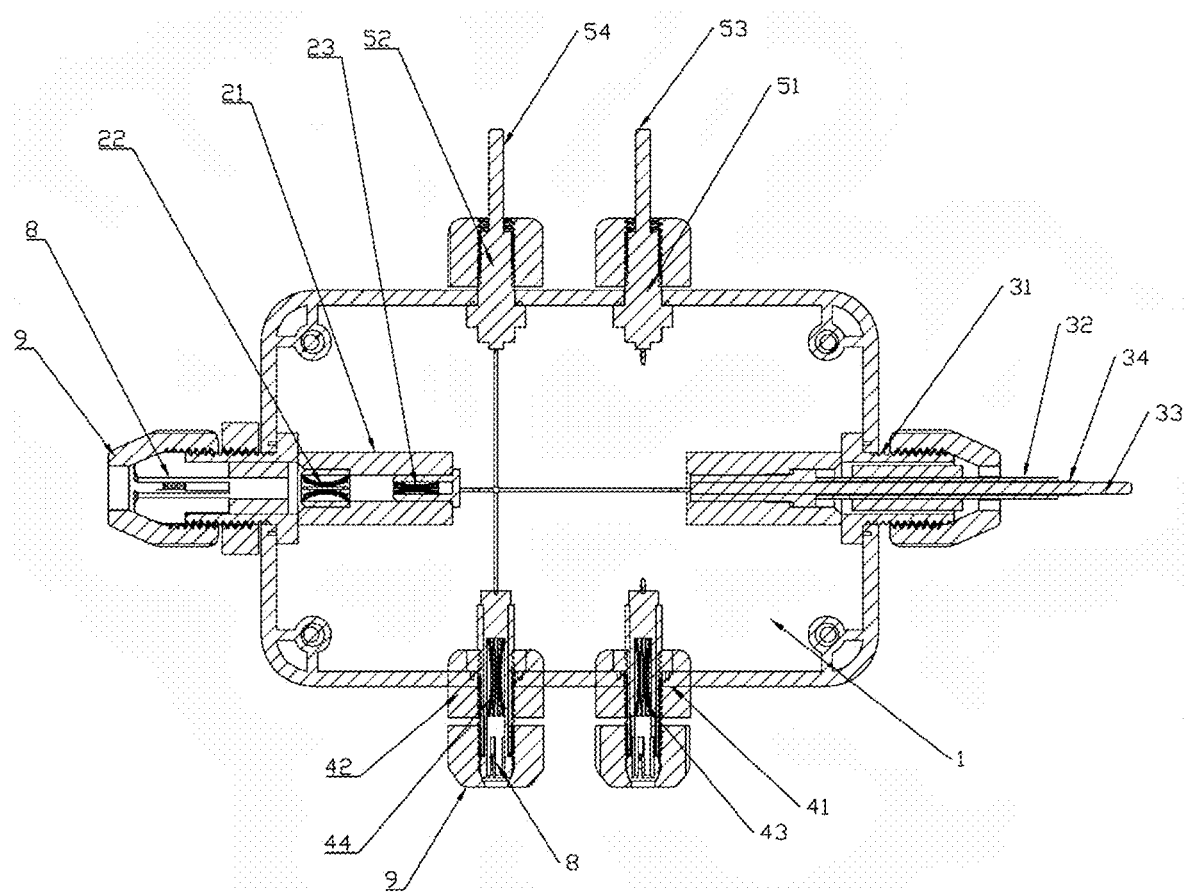
FIG. 6 is a sectional view of an overall structure of the present invention.
Figure 7:
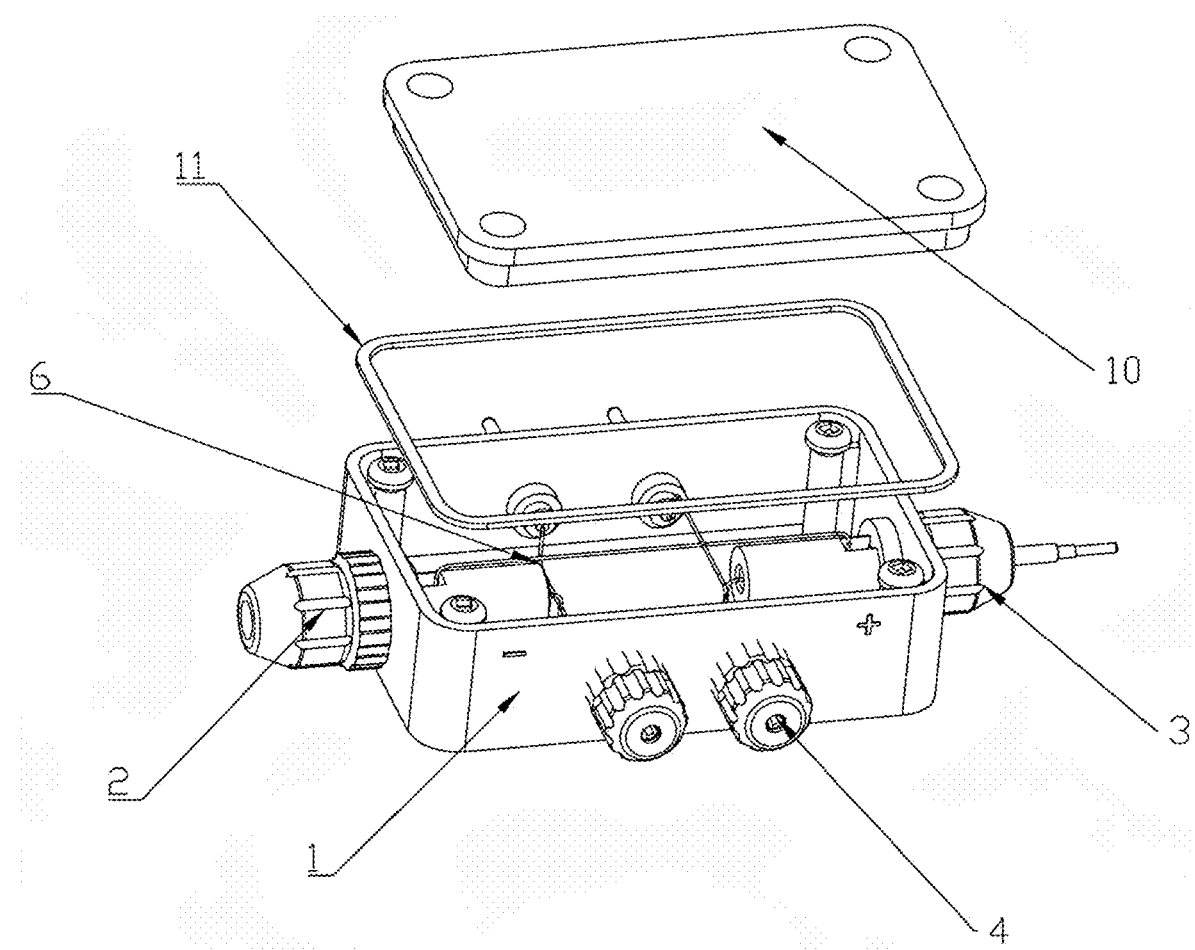
FIG. 7 is an exploded view of an overall structure of the present invention.
Figure 8:
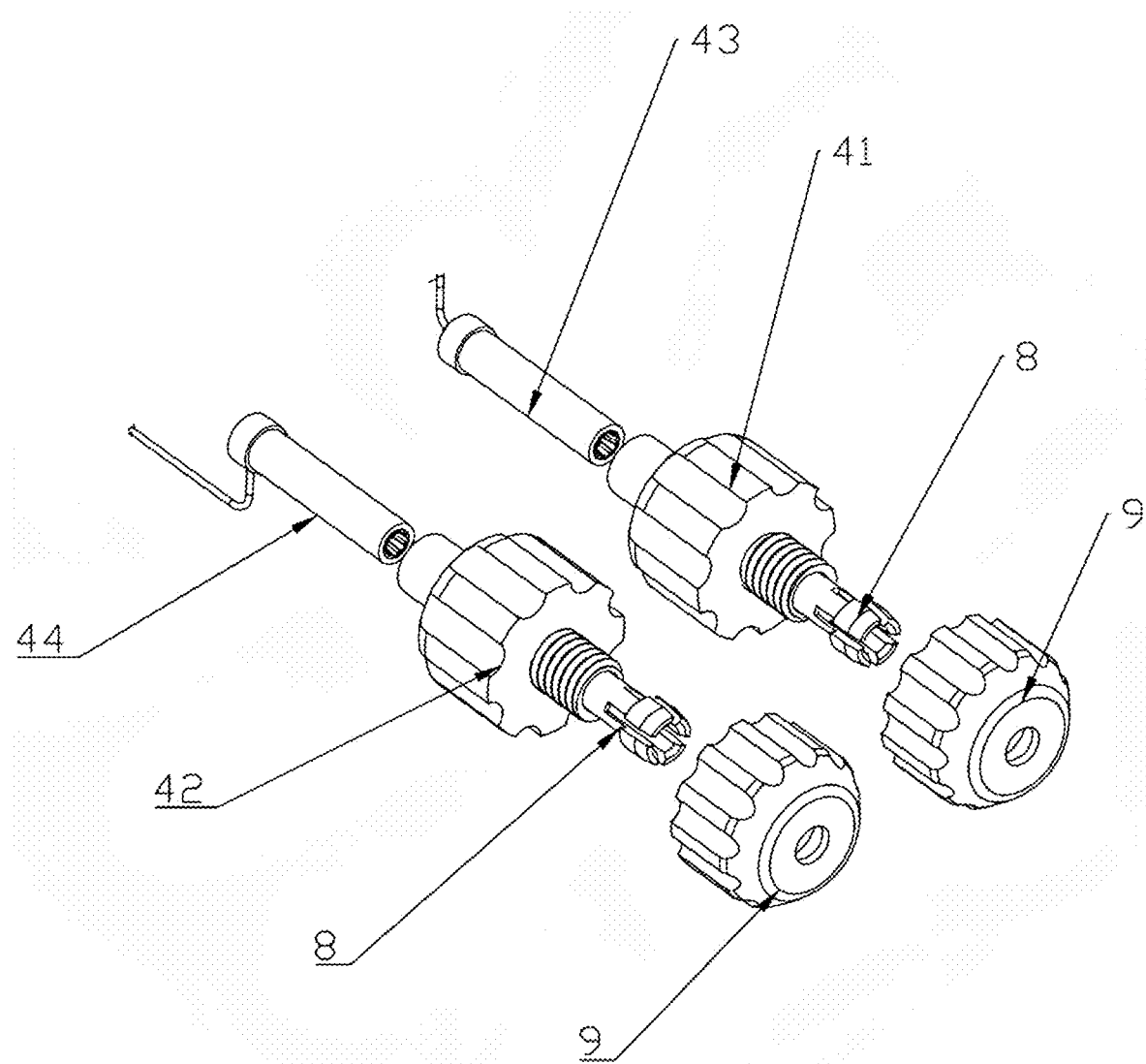
FIG. 8 is an exploded view of a temporary electrode female connector of the present invention.
Figure 9:
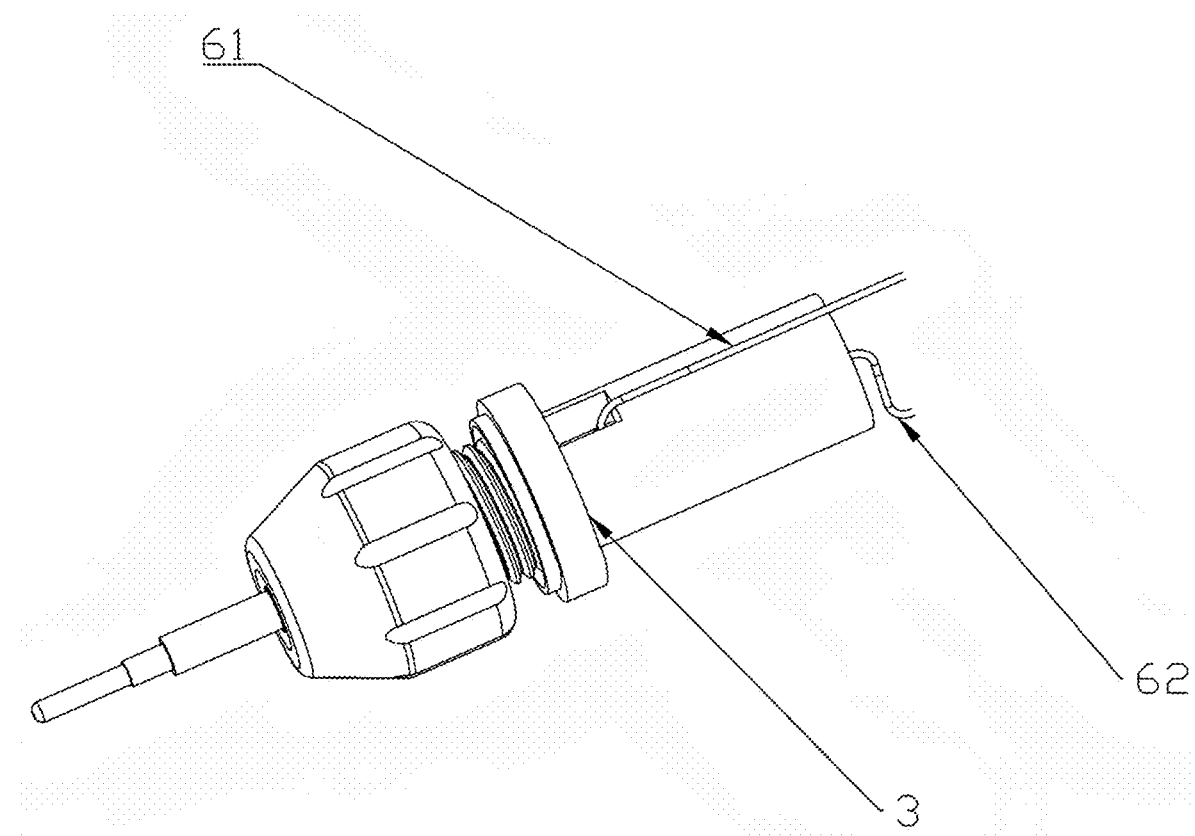
FIG. 9 is a schematic structural diagram of a permanent electrode male connector of the present invention.
Figure 10:
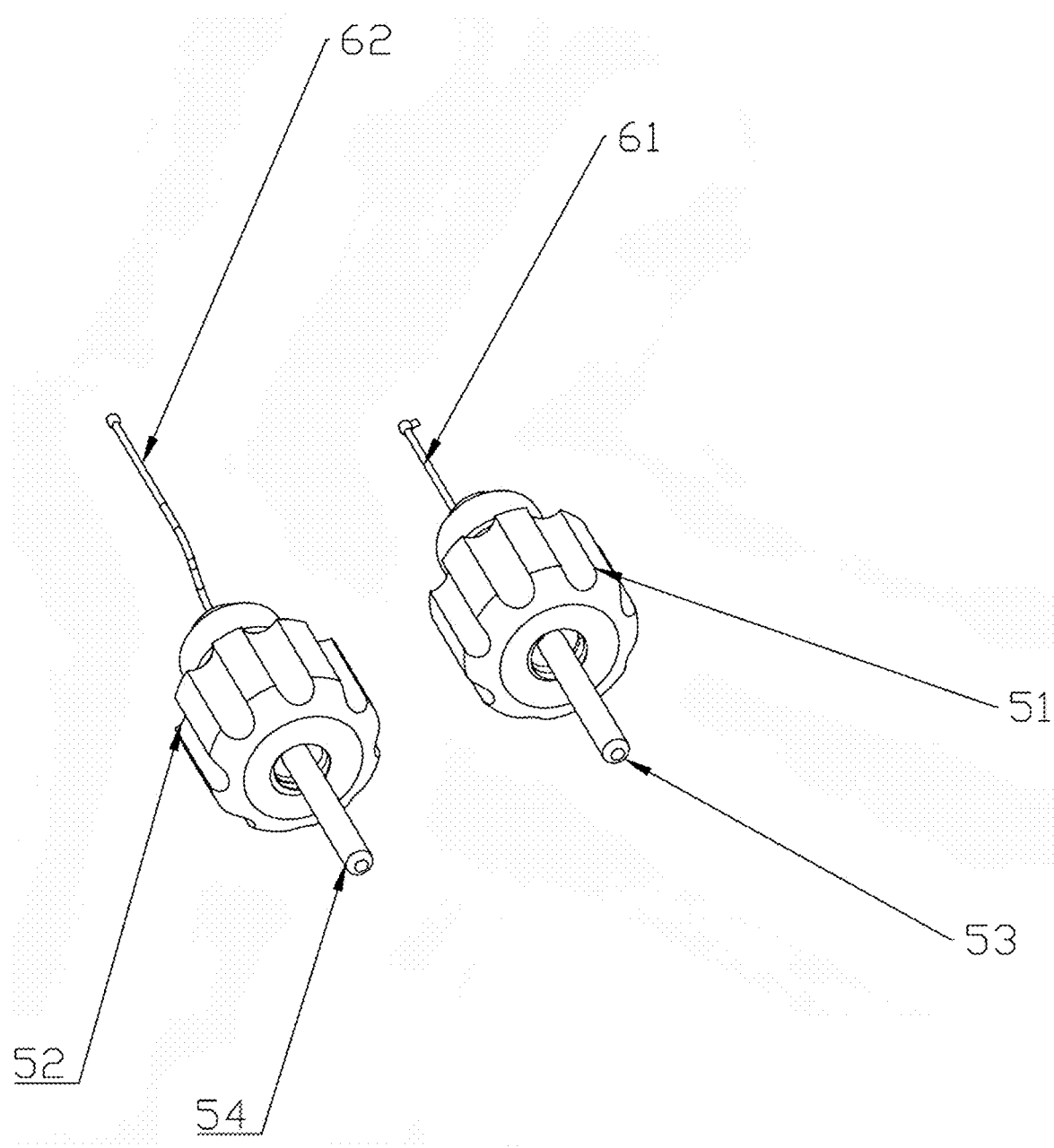
FIG. 10 is a schematic structural diagram of a temporary electrode male connector of the present invention.

Referring to FIG. 1 to FIG. 10, the present invention is a multifunctional pacemaker wire conversion device, where a permanent pacemaker and a temporary pacemaker can be freely combined with a permanent electrode or a temporary electrode for use, and the device includes a box body 1, a permanent electrode female connector 2, a permanent electrode male connector 3, a temporary electrode female connector 4, a temporary electrode male connector 5, and a circuit line 6. A cavity is formed in the box body 1, the permanent electrode female connector 2, the permanent electrode male connector 3, the temporary electrode female connector 4, and the temporary electrode male connector 5 are disposed on the box body 1, and the permanent electrode female connector 3, the permanent electrode male connector 2, the temporary electrode female connector 5, and the temporary electrode male connector 4 are electrically connected to each other through the circuit line 6 disposed in the cavity. The permanent electrode female connector 2 is configured to be connected to a permanent electrode. The permanent electrode male connector 3 is configured to be connected to a permanent pacemaker. The temporary electrode female connector 4 is configured to be connected to a temporary electrode. The temporary electrode male connector 5 is configured to be connected to a temporary pacemaker. During use, any one of the permanent pacemaker and the temporary pacemaker and any one of the permanent electrode and the temporary electrode are connected to the multifunctional pacemaker wire conversion device, so that the permanent pacemaker and the temporary pacemaker can be freely combined with the permanent electrode or the temporary electrode for use through the multifunctional pacemaker wire conversion device.

In the embodiment, the circuit line 6 includes a positive crosslink point 61 and a negative crosslink point 62. Positive electrodes of the permanent electrode male connector 3, the permanent electrode female connector 2, the temporary electrode male connector 5, and the temporary electrode female connector 4 are electrically connected through the positive crosslink point 61. Negative electrodes of the permanent electrode male connector 3, the permanent electrode female connector 2, the temporary electrode male connector 5, and the temporary electrode female connector 4 are electrically connected through the negative crosslink point 62. Specifically, the permanent electrode male connector 3, the permanent electrode female connector 2, the temporary electrode male connector 5, and the temporary electrode female connector 4 are sequentially connected in parallel through the positive crosslink point 61 and the negative crosslink point 62. During use, when a pacemaker (that is, the permanent pacemaker or the temporary pacemaker) and an electrode (that is, the permanent electrode or the temporary electrode) are connected to corresponding connectors on the multifunctional pacemaker wire conversion device, the two connectors are communicated under actions of the positive crosslink point 61 and the negative crosslink point 62 and form a loop.

In the embodiment, the permanent electrode female connector 2 includes a permanent electrode female connector fixing member 21, a permanent electrode female connector positive terminal 22, and a permanent electrode female connector negative terminal 23. The permanent electrode female connector fixing member 21 is fixed on the box body 1, the permanent electrode female connector fixing member 21 is of a tubular structure, a first end of the permanent electrode female connector fixing member 21 is placed in the cavity, and a second end of the permanent electrode female connector fixing member 21 is placed outside the box body 1. The permanent electrode female connector positive terminal 22 and the permanent electrode female connector negative terminal 23 are sequentially disposed in the permanent electrode female connector fixing member 21, a structure of the permanent electrode female connector 2 is similar to a structure of a socket connector configured to be connected to the permanent electrode on the permanent pacemaker, the permanent electrode female connector positive terminal 22 is connected to the positive crosslink point 61, and the permanent electrode female connector negative terminal 23 is connected to the negative crosslink point 62. When the permanent electrode is inserted from the second end of the permanent electrode female connector fixing member 21, the permanent electrode female connector positive terminal 22 is in contact with and is electrically connected to a positive electrode of the permanent electrode, and the permanent electrode female connector negative terminal 23 is in contact with and is electrically connected to a negative electrode of the permanent electrode, so that the permanent electrode can be electrically connected to the multifunctional pacemaker wire conversion device.

In the embodiment, the permanent electrode male connector 3 includes a permanent electrode male connector fixing member 31, a permanent electrode male connector positive terminal 32, and a permanent electrode male connector negative terminal 33. The permanent electrode male connector fixing member 31 is fixed on the box body 1, the permanent electrode male connector fixing member 31 is of a tubular structure, a first end of the permanent electrode male connector fixing member 31 is placed in the cavity, and a second end of the permanent electrode male connector fixing member 31 extends out of the box body 1. The permanent electrode male connector positive terminal 32 and the permanent electrode male connector negative terminal 33 are coaxially disposed in the permanent electrode male connector fixing member 31, and the permanent electrode male connector positive terminal 32 and the permanent electrode male connector negative terminal 33 are separated through an insulating layer 34. One end of each of the permanent electrode male connector positive terminal 32 and the permanent electrode male connector negative terminal 33 is fixedly disposed at the first end of the permanent electrode male connector fixing member 31, and the other end of each of the permanent electrode male connector positive terminal 32 and the permanent electrode male connector negative terminal 33 extends out of the box body 1 from the second end of the permanent electrode male connector fixing member 31 and forms a plug with a structure similar to that of the permanent electrode. The positive crosslink point 61 is connected to the permanent electrode male connector positive terminal 32, and the negative crosslink point 62 is connected to the permanent electrode male connector negative terminal 33. During use, a medical worker may directly insert the multifunctional pacemaker wire conversion device into a socket of the permanent pacemaker through the plug, so that the multifunctional pacemaker wire conversion device and the permanent pacemaker are electrically connected.

In the embodiment, the temporary electrode female connector 4 includes a temporary electrode female connector positive terminal fixing member 41, a temporary electrode female connector negative terminal fixing member 42, a temporary electrode female connector positive terminal 43, and a temporary electrode female connector negative terminal 44. Both the temporary electrode female connector positive terminal fixing member 41 and the temporary electrode female connector negative terminal fixing member 42 are fixed on the box body 1, the temporary electrode female connector positive terminal fixing member 41 and the temporary electrode female connector negative terminal fixing member 42 are of a tubular structure, first ends of the temporary electrode female connector positive terminal fixing member 41 and the temporary electrode female connector negative terminal fixing member 42 are placed in the cavity, and second ends of the temporary electrode female connector positive terminal fixing member 41 and the temporary electrode female connector negative terminal fixing member 42 extend out of the box body 1. The temporary electrode female connector positive terminal 43 is disposed in the temporary electrode female connector positive terminal fixing member 41 and is electrically connected to the positive crosslink point. The temporary electrode female connector negative terminal 44 is disposed in the temporary electrode female connector negative terminal fixing member 42 and is electrically connected to the negative crosslink point 62. When the temporary electrode is inserted from the second ends of the temporary electrode female connector positive terminal fixing member 41 and the temporary electrode female connector negative terminal fixing member 42, the temporary electrode female connector positive terminal 43 is in contact with a positive electrode of the temporary electrode, and the temporary electrode female connector negative terminal 44 is in contact with a negative electrode of the temporary electrode, so that the temporary electrode can be inserted into the multifunctional pacemaker wire conversion device and electrically connected to the multifunctional pacemaker wire conversion device.

In the embodiment, the temporary electrode male connector 5 includes a temporary electrode male connector positive terminal fixing member 51, a temporary electrode male connector negative terminal fixing member 52, a temporary electrode male connector positive terminal 53, and a temporary electrode male connector negative terminal 54. Both the temporary electrode male connector positive terminal fixing member 51 and the temporary electrode male connector negative terminal fixing member 52 are disposed on the box body 1. One end of the temporary electrode male connector positive terminal 53 is fixedly disposed on the temporary electrode male connector positive terminal fixing member 51, and the other end of the temporary electrode male connector positive terminal 53 extends out of the box body 1. One end of the temporary electrode male connector negative terminal 54 is fixedly disposed on the temporary electrode male connector negative terminal fixing member 52, and the other end of the temporary electrode male connector negative terminal 54 extends out of the box body 1, so that a plug connected to the temporary pacemaker can be formed. In addition, the positive crosslink point 61 is electrically connected to the temporary electrode male connector positive terminal 53, and the negative electrode is electrically connected to the temporary electrode male connector negative terminal 54, so that the temporary electrode male connector positive terminal 53 and the temporary electrode male connector negative terminal 54 can be connected to another connector in parallel through the positive crosslink point 61 and the negative crosslink point 62.

In the embodiment, the permanent electrode female connector positive terminal 22, the permanent electrode female connector negative terminal 23, the temporary electrode female connector positive terminal 43, and the temporary electrode female connector negative terminal 44 are all of an annular structure. A plurality of groups of first elastic sheets 7 are disposed on an inner side wall of the annular structure (that is, the permanent electrode female connector positive terminal 22, the permanent electrode female connector negative terminal 23, the temporary electrode female connector positive terminal 43, and the temporary electrode female connector negative terminal 44), and the plurality of groups of first elastic sheets 7 are disposed along a circumference of the annular structure, so that an electrode in a corresponding connector can be in contact with the permanent electrode or the temporary electrode through the first elastic sheets 7 after the permanent electrode or the temporary electrode is inserted into the corresponding connector, thereby improving stability of current transmission between the permanent electrode or the temporary electrode and the corresponding connector and universal compatibility of the permanent electrode or the temporary electrode inserted into the corresponding connector.

Specifically, in actual application, the first elastic sheets 7 may be specifically divided into a permanent electrode female connector positive terminal elastic sheet disposed on the permanent electrode female connector positive terminal 22, a permanent electrode female connector negative terminal elastic sheet disposed on the permanent electrode female connector negative terminal 23, a temporary electrode female connector positive terminal elastic sheet disposed on the temporary electrode female connector positive terminal 43, and a temporary electrode female connector negative terminal elastic sheet disposed on the temporary electrode female connector negative terminal 44.

In the embodiment, the device further includes an elastic collet 8 and a cover cap 9. The elastic collet 8 is also referred to as an elastic collet head or a cylindrical collet and is a cylindrical clamp for locking parts. The elastic collet 8 is disposed at the second end of each of the permanent electrode female connector fixing member 21, the temporary electrode female connector positive terminal fixing member 41, and the temporary electrode female connector negative terminal fixing member 42. An outer wall of each of the permanent electrode female connector fixing member 21, the temporary electrode female connector positive terminal fixing member 41, and the temporary electrode female connector negative terminal fixing member 42 is provided with a thread. The cover cap 9 is detachably disposed on each of the permanent electrode female connector fixing member 21, the temporary electrode female connector positive terminal fixing member 41, and the temporary electrode female connector negative terminal fixing member 42 through the thread. When the temporary electrode or the permanent electrode is inserted into the corresponding connector on the multifunctional pacemaker wire conversion device, the cover cap 9 is placed on the permanent electrode female connector fixing member 21, the temporary electrode female connector positive terminal fixing member 41, or the temporary electrode female connector negative terminal fixing member 42. The elastic collet is a cylindrical clamp composed of a plurality of collet sheets generally. At this time, the cover cap 9 abuts against the elastic collet 8, so that the collet sheets of the elastic collet 8 contract towards a central axial direction of the elastic collet under an action of the cover cap 9, thereby enabling the elastic collet 8 to clamp the permanent electrode or the temporary electrode. Therefore, the permanent electrode or the temporary electrode can be fixed on the corresponding connector on the multifunctional pacemaker wire conversion device more firmly.

In the embodiment, the device further includes an end cover 10 and a sealing ring 11. The end cover 10 is detachably disposed on the box body 1, to close the cavity in the box body 1, thereby preventing the circuit line in the cavity from exposing to the outside, so that security of the multifunctional pacemaker wire conversion device during use is greatly increased. In addition, the sealing ring is further disposed between the end cover 10 and the box body 1. When the end cover 10 is detachably disposed on the box body 1, the end cover 10 abuts against the sealing ring 11. At this time, under an action of the sealing ring 11, the cavity in the box body 1 forms a closed waterproof chamber, so that external liquid may be effectively prevented from penetrating into the cavity from a gap between the box body 1 and the end cover 10 to affect the circuit line in the cavity, thereby further increasing the security of the multifunctional pacemaker wire conversion device during use.

To further highlight core innovation of the present invention to support the technical problems to be solved in the present invention, the followings are supplementary explanations of the technical solutions provided in the present invention by listing various application scenarios of the present invention:

As an application scenario of the present invention, the present invention further discloses a method for converting a single-chamber pacing into a dual-chamber pacemaker.

The dual-chamber pacemaker is a medical apparatus for treating an abnormal cardiac rhythm, which is composed of one permanent pacemaker and two permanent electrodes. The permanent electrodes are inserted into a heart through a vein and transmit an electrical signal to different parts of the heart, to maintain a normal cardiac rhythm. Compared with traditional single-chamber pacing, the dual-chamber pacemaker has higher accuracy and adaptability, which may better simulate an electrical activity of a normal heart and improve a therapeutic effect by stimulating a plurality of cardiomyocytes simultaneously. In addition, the dual-chamber pacemaker may further be personalized according to a specific condition of a patient, to implement an optimal therapeutic effect. However, when a battery of the single-chamber pacemaker of the patient is exhausted and the patient is pacemaker-dependent, the single-chamber pacemaker may not be able to simulate the electrical activity of the heart normally. Therefore, a new permanent pacemaker needs to be replaced. With the development of science and technology, the single-chamber pacemaker gradually develops into the dual-chamber pacemaker that can better simulate the normal cardiac rhythm. Therefore, when the battery of the single-chamber pacemaker of the patient is exhausted and the new permanent pacemaker is replaced, a decision of replacing the original single-chamber pacemaker of the patient with the dual-chamber pacemaker is made according to the specific condition of the patient and an advice of a doctor, to better simulate the electrical activity of the normal heart, to improve living quality of the patient.

Specifically, a first permanent electrode and a first permanent pacemaker (that is, the single-chamber pacemaker) connected to the first permanent electrode are implanted into a body of the patient. In the method for converting a single-chamber pacemaker into a dual-chamber pacemaker disclosed in the present invention, the multifunctional pacemaker wire conversion device according to any one of the above is applied. The method is used to convert the original first pacemaker (that is, the single-chamber pacemaker) into the dual-chamber pacemaker when the battery of the pacemaker of the patient that is pacemaker-dependent is exhausted, and specific steps are as follows:

1. Preoperative preparation: including performing detailed cardiac evaluation on a heart of the patient through electrocardiogram, cardiac ultrasound, and another means, to determine a cardiac condition of the patient; and selecting a model of the dual-chamber pacemaker and an adapted second permanent electrode according to a cardiac evaluation result of the patient;
2. Local anesthesia: performing local anesthesia on an operative region, to relieve pain of the patient;
3. Original permanent pacemaker removal: exposing the first permanent pacemaker implanted into the body of the patient through an incision; and
first connecting a temporary pacemaker to a temporary electrode male connector 5 of the multifunctional pacemaker wire conversion device, and then connecting the first permanent electrode to a permanent electrode female connector 2 of the multifunctional pacemaker wire conversion device after disconnecting the permanent electrode from the first permanent pacemaker, so that the first permanent electrode can be connected to the temporary pacemaker through the multifunctional pacemaker wire conversion device more quickly;
4. New permanent pacemaker implantation: implanting the second permanent electrode into the heart of the patient, where it should be noted that a venous channel needs to be reopened when the second permanent electrode is implanted into the heart of the patient; testing a working state of the second permanent electrode; and if the working state of the second permanent electrode is normal, connecting the second permanent electrode to the dual-chamber pacemaker; then disconnecting the first permanent electrode from the multifunctional pacemaker wire conversion device, and removing the temporary pacemaker and the multifunctional pacemaker wire conversion device; and
testing a working state of the first permanent electrode; and connecting the tested first permanent electrode to the dual-chamber pacemaker;
5. Parameter setting and function testing of the permanent pacemaker: setting a parameter of the dual-chamber pacemaker, to adapt to the cardiac condition of the patient; and
testing a function of the dual-chamber pacemaker, to ensure that the dual-chamber pacemaker can effectively perform temporary pacing on the heart; and
6. Incision suturing: after it is determined that the dual-chamber pacemaker works normally, burying the dual-chamber pacemaker in the body of the patient, and suturing the incision.

As another application scenario of the present invention, the present invention further discloses a method for converting a single-chamber pacemaker into a cardiac resynchronization therapy pacemaker. Cardiac resynchronization therapy (CRT for short) is a non-drug therapy method for treating cardiac failure. A special pacemaker is implanted between two cardiac ventricles of a heart, to improve a contraction function and coordination of the heart, thereby improving living quality and prognosis of a patient.

The cardiac resynchronization therapy pacemaker is mainly used to adjust a contraction rhythm of the heart through electrical stimulation, to enable left and right cardiac ventricles to contract simultaneously, thereby avoiding a decline in a cardiac function caused by uncoordinated cardiac ventricle contraction. In addition, the CRT may further reduce cardiac load and reduce myocardial oxygen consumption, thereby alleviating symptoms and prolonging a survival period of the patient.

Converting the single-chamber pacemaker into the cardiac resynchronization therapy pacemaker is suitable for those patients with heart failure, left bundle-branch block, or intraventricular conduction delays. Through the multifunctional pacemaker wire conversion device according to any one of the above, an original single-chamber pacemaker (that is, a first permanent pacemaker) of the patient is replaced with a new cardiac resynchronization therapy pacemaker.

Specific steps are as follows:
1. Preoperative preparation: including performing detailed cardiac evaluation on a heart of the patient through electrocardiogram, cardiac ultrasound, and another means, to determine a cardiac condition of the patient; and selecting a model of the cardiac resynchronization therapy pacemaker and an adapted third permanent electrode according to a cardiac evaluation result of the patient;
2. Local anesthesia: performing local anesthesia on an operative region, to relieve pain of the patient;
3. Original permanent pacemaker removal: exposing the first permanent pacemaker implanted into the body of the patient through an incision; and
first connecting a temporary pacemaker to a temporary electrode male connector 5 of the multifunctional pacemaker wire conversion device, and then connecting the first permanent electrode to a permanent electrode female connector 2 of the multifunctional pacemaker wire conversion device after disconnecting the permanent electrode from the first permanent pacemaker, so that the first permanent electrode can be connected to the temporary pacemaker through the multifunctional pacemaker wire conversion device more quickly;

4. New permanent pacemaker implantation: implanting the third permanent electrode into the heart of the patient, and testing a working state of the third permanent electrode; and if the working state of the third permanent electrode is normal, connecting the third permanent electrode to the cardiac resynchronization therapy pacemaker, where it should be noted that a venous channel needs to be reopened when the third permanent electrode is implanted into the heart of the patient;

then disconnecting the first permanent electrode from the multifunctional pacemaker wire conversion device, and removing the temporary pacemaker and the multifunctional pacemaker wire conversion device; and testing a working state of the first permanent electrode; and connecting the tested first permanent electrode to the cardiac resynchronization therapy pacemaker;

5. Parameter setting and function testing of the permanent pacemaker: setting a parameter of the cardiac resynchronization therapy pacemaker, to adapt to the cardiac condition of the patient; and testing a function of the cardiac resynchronization therapy pacemaker, to ensure that the cardiac resynchronization therapy pacemaker can effectively perform temporary pacing on the heart; and 6. Incision suturing: after it is determined that the cardiac resynchronization therapy pacemaker works normally, burying the cardiac resynchronization therapy pacemaker in the body of the patient, and suturing the incision.

Since the permanent pacemaker may be exposed due to infection, mechanical factors, skin of the patient, and the like after the permanent pacemaker is implanted into the patient, after the above permanent pacemaker is exposed, a medical worker reimplants the permanent pacemaker into the body of the patient after detecting that a function of the permanent pacemaker is normal. Therefore, the present invention further discloses a method for reimplanting a permanent pacemaker, where the multifunctional pacemaker wire conversion device according to any one of the above is applied, and the exposed pacemaker is reimplanted into the body of the patient.

Specific steps include:

exposing a first permanent pacemaker implanted into a pocket of a patient through an incision;

first connecting a temporary pacemaker to a temporary electrode male connector of the multifunctional pacemaker wire conversion device, then disconnecting a permanent electrode from the first permanent pacemaker, and connecting a first permanent electrode to a permanent electrode female connector of the multifunctional pacemaker wire conversion device;

performing a debridement treatment on the pocket of the patient;

performing a disinfection treatment on the first permanent pacemaker;

disconnecting the first permanent electrode from the multifunctional pacemaker wire conversion device, removing the temporary pacemaker and the multifunctional pacemaker wire conversion device, and reconnecting the first permanent pacemaker to the first permanent electrode; and reburying the first permanent pacemaker in the pocket of the patient, and suturing the incision.

During actual use, it is found that after the permanent pacemaker is implanted into some patients, the patients may have allergic reactions to a material of the permanent pacemaker. Therefore, when the patient has allergic reactions to the material of the permanent pacemaker, the patient needs to be treated urgently, and a new permanent pacemaker needs to be replaced, to eliminate an allergen in the body of the patient. Therefore, as another application scenario of the present invention, the present invention further discloses an emergency treatment method when a patient is allergic to a permanent pacemaker, where the multifunctional pacemaker wire conversion device according to any one of the above is applied, to perform an emergency treatment on the patient and assist in replacing a new permanent pacemaker.

Specific steps include:

exposing a first permanent pacemaker implanted into a pocket of a patient through an incision;

first connecting a temporary pacemaker to a temporary electrode male connector of the multifunctional pacemaker wire conversion device, then disconnecting a permanent electrode from the first permanent pacemaker, and connecting a first permanent electrode to a permanent electrode female connector of the multifunctional pacemaker wire conversion device;

debriding the pocket of the patient, and checking an allergen of the patient;

customizing a new fourth permanent electrode according to the allergen of the patient;

disconnecting the first permanent electrode from the multifunctional pacemaker wire conversion device, removing the temporary pacemaker and the multifunctional pacemaker wire conversion device, and connecting the first permanent electrode to a new fourth permanent pacemaker;

setting a parameter of the fourth permanent pacemaker, to adapt to the cardiac condition of the patient;

testing a function of the fourth permanent pacemaker, to ensure that the fourth permanent pacemaker paces the heart; and after it is determined that the fourth permanent pacemaker works normally, reburying the fourth permanent pacemaker in the pocket of the patient, and suturing the incision.

As a further application scenario of the present invention, the present invention further discloses a method for using a permanent pacemaker in temporary cardiac pacing of a patient.

Specifically:

a temporary pacemaker is usually used for short-term therapy, for example, during waiting for an implantation operation of a permanent pacemaker or during an acute arrhythmia episode, which may help maintain a stable heart rate, to ensure that blood can flow normally to all parts of a body. Since a thigh vein is large and close to a heart, and insertion is relatively easy, the temporary pacemaker is usually inserted through the thigh vein. In an operating room, a doctor inserts a thin and long temporary into the thigh vein under local anesthesia and then guides the temporary electrode to the inside of the heart, while a tail end of the temporary electrode stays outside the body of the patient and is connected to a temporary pacemaker. The temporary pacemaker is relatively large in volume, especially for an infant and a young child, who need to be held by another caregiver during daily activities. Therefore, a larger temporary pacemaker is not convenient for the caregiver to carry. Therefore, in the present invention, after the temporary electrode is implanted into the body of the patient, one end, placed outside the body of the patient, of the temporary electrode is connected to a temporary electrode female connector 4 of the multifunctional pacemaker wire conversion device according to any one of the above, and the permanent pacemaker is connected to a permanent electrode male connector 3 of the multifunctional pacemaker wire conversion device, so that the permanent pacemaker can send an electrical pulse to the temporary electrode through the multifunctional pacemaker wire conversion device.

The specific method includes the following steps:

performing local infiltration anesthesia near a puncture point, performing femoral vein puncture with a puncture needle, implanting a guide wire in a femoral vein, and delivering a vascular sheath into the femoral vein;

delivering one end of the temporary electrode into the heart through the vascular sheath, and placing the other end outside the body of the patient;

electrically connecting one end, placed outside the body of the patient, of the temporary electrode to the temporary electrode female connector of the multifunctional pacemaker wire conversion device; and connecting the permanent pacemaker to the permanent electrode male connector of the multifunctional pacemaker wire conversion device;

setting a parameter of the permanent pacemaker, to adapt to a cardiac condition of the patient;

testing a function of the permanent pacemaker, to ensure that the permanent pacemaker can effectively perform temporary pacing on the heart; and after it is determined that the permanent pacemaker works normally, fixing the temporary electrode and the permanent pacemaker, to avoid displacement.

It should be emphasized that the above various applicable scenarios are merely several common scenarios of the multifunctional pacemaker wire conversion device provided in the present invention, and are not intended to limit the usage of the multifunctional pacemaker wire conversion device provided in the present invention to the above scenarios. In other words, as long as the multifunctional pacemaker wire conversion device provided in the present invention is applied in application scenarios for conversion between pacemakers, the application scenarios are applicable to the present invention and are within the protection scope of the present invention.

As a supplementary explanation, according to the multifunctional pacemaker wire conversion device provided in the present invention, the temporary pacemaker can be externally connected through the conversion device when a permanent pacing electrode is implanted into the body of the patient, and the permanent pacemaker can be externally connected through the conversion device when the temporary pacemaker has been implanted into the patient.

In a first application environment, when the permanent pacing electrode is implanted into the body of the patient, the temporary pacemaker is externally connected through the conversion device. An advantage is that the permanent pacing electrode implanted into the body may be implanted via an internal jugular vein, a subclavian vein, or an axillary vein. Compared with a temporary pacing electrode, the permanent pacing electrode is more stable in position and more rational in parameter, which may be used in a patient who needs a longer temporary pacing transition (for example, several weeks or months), for example, a patient waiting for cardiac transplantation, to obtain a more stable pacing parameter. At this time, the multifunctional pacemaker wire conversion device provided in the present invention may connect the permanent pacing electrode to the temporary pacemaker externally.

In a second application scenario, when the temporary pacemaker has been implanted into the patient, the permanent pacemaker is externally connected through the conversion device. An advantage is that for some patients who need a long time for a temporary pacing transition, if the temporary pacing electrode has been implanted, but the patients cannot tolerate long-term bed rest and need to move around, since the temporary pacemaker is bulky, the temporary pacemaker is inconvenient to wear. At this time, the multifunctional pacemaker wire conversion device provided in the present invention may connect the temporary pacemaker to the permanent pacemaker externally.

The above disclosure is only some specific embodiments of the present invention, but the present invention is not limited thereto, and any changes that can be thought of by a person skilled in the art should fall within the protection scope of the present invention.

What is claimed is:

1. A multifunctional pacemaker wire conversion device, wherein a permanent pacemaker and a temporary pacemaker can be freely combined with a permanent electrode or a temporary electrode for use, and the device comprises:

a box body (1), wherein a cavity is formed in the box body (1);

a permanent electrode female connector (2), disposed on the box body (1) and configured to be connected to the permanent electrode, wherein the permanent electrode female connector (2) comprises a positive terminal (22) and a negative terminal (23);

a permanent electrode male connector (3), disposed on the box body (1) and configured to be connected to the permanent pacemaker, wherein the permanent electrode male connector (3) comprises a positive terminal (32) and a negative terminal (33);

a temporary electrode female connector (4), disposed on the box body (1) and configured to be connected to the temporary electrode, wherein the temporary electrode female connector (4) comprises a positive terminal (43) and a negative terminal (44);

a temporary electrode male connector (5), disposed on the box body (1) and configured to be connected to the temporary pacemaker, wherein the temporary electrode male connector (5) comprises a positive terminal (53) and a negative terminal (54); and a circuit line (6), disposed in the cavity, wherein the circuit line (6) comprises a positive crosslink point (61) and a negative crosslink point (62), wherein the positive terminals (22, 32, 43, 53) are electrically connected to the positive crosslink point (61), and the negative terminals (23, 33, 44, 54) are electrically connected to the negative crosslink point (62).

2. The multifunctional pacemaker wire conversion device according to claim 1, wherein the circuit line (6) comprises:

the positive crosslink point (61), wherein the positive electrodes of the permanent electrode male connector (3), the permanent electrode female connector (2), the temporary electrode male connector (5), and the temporary electrode female connector (4) are electrically connected through the positive crosslink point (61); and the negative crosslink point (62), wherein the negative electrodes of the permanent electrode male connector (3), the permanent electrode female connector (2), the temporary electrode male connector (5), and the temporary electrode female connector (4) are electrically connected through the negative crosslink point (62).

3. The multifunctional pacemaker wire conversion device according to claim 2, wherein
the permanent electrode female connector (2) comprises a permanent electrode female connector fixing member (21), a permanent electrode female connector positive terminal (22), and a permanent electrode female connector negative terminal (23); the permanent electrode female connector fixing member (21) is fixed on the box body (1), the permanent electrode female connector fixing member (21) is of a tubular structure, a first end of the permanent electrode female connector fixing member (21) is placed in the cavity, and a second end of the permanent electrode female connector fixing member (21) is placed outside the box body (1); the permanent electrode female connector positive terminal (22) and the permanent electrode female connector negative terminal (23) are sequentially disposed in the permanent electrode female connector fixing member (21), the permanent electrode female connector positive terminal (22) is connected to the positive crosslink point (61), and the permanent electrode female connector negative terminal (23) is connected to the negative crosslink point (62); and when the permanent electrode is inserted from the second end of the permanent electrode female connector fixing member (21), the permanent electrode female connector positive terminal (22) is in contact with and is electrically connected to a positive electrode of the permanent electrode, and the permanent electrode female connector negative terminal (23) is in contact with and is electrically connected to a negative electrode of the permanent electrode; and the permanent electrode male connector (3) comprises a permanent electrode male connector fixing member (31), a permanent electrode male connector positive terminal (32), and a permanent electrode male connector negative terminal (33); the permanent electrode male connector fixing member (31) is fixed on the box body (1), the permanent electrode male connector fixing member (31) is of a tubular structure, a first end of the permanent electrode male connector fixing member (31) is placed in the cavity, and a second end of the permanent electrode male connector fixing member (31) extends out of the box body (1); the permanent electrode male connector positive terminal (32) and the permanent electrode male connector negative terminal (33) are coaxially disposed in the permanent electrode male connector fixing member (31), and the permanent electrode male connector positive terminal (32) and the permanent electrode male connector negative terminal (33) are separated through an insulating layer (34); one end of each of the permanent electrode male connector positive terminal (32) and the permanent electrode male connector negative terminal (33) is fixedly disposed at the first end of the permanent electrode male connector fixing member (31), and the other end of each of the permanent electrode male connector positive terminal (32) and the permanent electrode male connector negative terminal (33) extends out of the box body (1) from the second end of the permanent electrode male connector fixing member (31); and the positive crosslink point (61) is connected to the permanent electrode male connector positive terminal (32), and the negative crosslink point (62) is connected to the permanent electrode male connector negative terminal (33).

4. The multifunctional pacemaker wire conversion device according to claim 3, wherein
the temporary electrode female connector (4) comprises a temporary electrode female connector positive terminal fixing member (41), a temporary electrode female connector negative terminal fixing member (42), a temporary electrode female connector positive terminal (43), and a temporary electrode female connector negative terminal (44); both the temporary electrode female connector positive terminal fixing member (41) and the temporary electrode female connector negative terminal fixing member (42) are fixed on the box body (1), the temporary electrode female connector positive terminal fixing member (41) and the temporary electrode female connector negative terminal fixing member (42) are of a tubular structure, first ends of the temporary electrode female connector positive terminal fixing member (41) and the temporary electrode female connector negative terminal fixing member (42) are placed in the cavity, and second ends of the temporary electrode female connector positive terminal fixing member (41) and the temporary electrode female connector negative terminal fixing member (42) extend out of the box body (1); the temporary electrode female connector positive terminal (43) is disposed in the temporary electrode female connector positive terminal fixing member (41) and is electrically connected to the positive electrode; the temporary electrode female connector negative terminal (44) is disposed in the temporary electrode female connector negative terminal fixing member (42) and is electrically connected to the negative crosslink point (62); and when the temporary electrode is inserted from the second ends of the temporary electrode female connector positive terminal fixing member (41) and the temporary electrode female connector negative terminal fixing member (42), the temporary electrode female connector positive terminal (43) is in contact with a positive electrode of the temporary electrode, and the temporary electrode female connector negative terminal (44) is in contact with a negative electrode of the temporary electrode; and the temporary electrode male connector (5) comprises a temporary electrode male connector positive terminal fixing member (51), a temporary electrode male connector negative terminal fixing member (52), a temporary electrode male connector positive terminal (53), and a temporary electrode male connector negative terminal (54); both the temporary electrode male connector positive terminal fixing member (51) and the temporary electrode male connector negative terminal fixing member (52) are fixed on the box body (1); one end of the temporary electrode male connector positive terminal (53) is fixedly disposed on the temporary electrode male connector positive terminal fixing member (51), and the other end of the temporary electrode male connector positive terminal (53) extends out of the box body (1); one end of the temporary electrode male connector negative terminal (54) is fixedly disposed on the temporary electrode male connector negative terminal fixing member (52), and the other end of the temporary electrode male connector negative terminal (54) extends out of the box body (1); and the positive crosslink point (61) is electrically connected to the temporary electrode male connector positive terminal (53), and the negative electrode is electrically connected to the temporary electrode male connector negative terminal (54).

5. The multifunctional pacemaker wire conversion device according to claim 4, wherein the permanent electrode female connector positive terminal (22), the permanent electrode female connector negative terminal (23), the temporary electrode female connector positive terminal (43), and the temporary electrode female connector negative terminal (44) are all of an annular structure, a plurality of groups of first elastic sheets (7) are disposed on an inner side wall of the annular structure, and the plurality of groups of first elastic sheets (7) are disposed along a circumference of the annular structure.

6. The multifunctional pacemaker wire conversion device according to claim 4, further comprising an elastic collet (8), a cover cap (9), an end cover (10), and a sealing ring (11), wherein
- the elastic collet (8) is disposed at the second end of each of the permanent electrode female connector fixing member (21), the temporary electrode female connector positive terminal fixing member (41), and the temporary electrode female connector negative terminal fixing member (42);
- an outer wall of each of the permanent electrode female connector fixing member (21), the temporary electrode female connector positive terminal fixing member (41), and the temporary electrode female connector negative terminal fixing member (42) is provided with a thread;
- the cover cap (9) is disposed on each of the permanent electrode female connector fixing member (21), the temporary electrode female connector positive terminal fixing member (41), and the temporary electrode female connector negative terminal fixing member (42) through the thread;
- when the cover cap (9) is disposed on the permanent electrode female connector fixing member (21), the temporary electrode female connector positive terminal fixing member (41), or the temporary electrode female connector negative terminal fixing member (42), the cover cap (9) abuts against the elastic collet (8), and the elastic collet (8) contracts under an action of the cover cap (9); and
- the end cover (10) is detachably disposed on the box body (1), the sealing ring (11) is disposed between the end cover (10) and the box body (1), and when the end cover (10) is detachably disposed on the box body (1), the end cover (10) abuts against the sealing ring (11), and the cavity forms a closed waterproof chamber.

* * * * *